(12) United States Patent
Melkant

(10) Patent No.: US 8,470,007 B2
(45) Date of Patent: Jun. 25, 2013

(54) ANTERO-LATERAL PLATING SYSTEMS AND METHODS FOR SPINAL STABILIZATION

(75) Inventor: Anthony J. Melkant, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/302,261

(22) Filed: Nov. 22, 2011

(65) Prior Publication Data

US 2012/0071924 A1 Mar. 22, 2012

Related U.S. Application Data

(63) Continuation of application No. 12/660,223, filed on Feb. 23, 2010, now Pat. No. 8,109,980, which is a continuation of application No. 11/109,164, filed on Apr. 19, 2005, now Pat. No. 7,678,113.

(51) Int. Cl.
*A61B 17/88* (2006.01)

(52) U.S. Cl.
USPC .......................................... 606/297

(58) Field of Classification Search
USPC ....................... 606/70, 71, 280–299
See application file for complete search history.

(56) References Cited

U.S. PATENT DOCUMENTS

| | | | |
|---|---|---|---|
| 3,659,595 A | 5/1972 | Haboush | |
| 3,695,259 A | 10/1972 | Yost | |
| 3,741,205 A | 6/1973 | Markolf et al. | |
| 4,488,543 A | 12/1984 | Tornier | |
| 4,794,918 A | 1/1989 | Wolter | |
| 4,938,769 A | 7/1990 | Shaw | |
| 4,944,757 A | 7/1990 | Martinez et al. | |
| 4,957,497 A | 9/1990 | Hoogland et al. | |
| 4,963,152 A | 10/1990 | Hofmann et al. | |
| 5,061,271 A | 10/1991 | Van Zile | |
| 5,127,914 A | 7/1992 | Calderale et al. | |
| 5,147,361 A | 9/1992 | Ojima et al. | |
| 5,324,290 A | 6/1994 | Zdeblick et al. | |
| 5,326,364 A * | 7/1994 | Clift et al. ................... | 623/21.11 |
| 5,397,363 A | 3/1995 | Gelbard | |
| 5,423,826 A | 6/1995 | Coates et al. | |
| 5,534,027 A | 7/1996 | Hodorek | |
| 5,549,612 A | 8/1996 | Yapp et al. | |
| 5,569,250 A | 10/1996 | Sarver et al. | |
| 5,601,553 A | 2/1997 | Trebing et al. | |
| 5,766,254 A | 6/1998 | Gelbard | |
| 5,785,713 A | 7/1998 | Jobe | |
| 5,800,433 A | 9/1998 | Benzel et al. | |
| 5,810,822 A * | 9/1998 | Mortier ....................... | 606/86 B |
| 5,879,389 A | 3/1999 | Koshino | |

(Continued)

FOREIGN PATENT DOCUMENTS

DE 19542116 A1 5/1997
EP 0455255 A1 11/1991

(Continued)

*Primary Examiner* — Eduardo C Robert
*Assistant Examiner* — Tara Carter

(57) ABSTRACT

A plating system for stabilization of a bony segment includes a plate engageable to at least first and second bony elements. For spinal stabilization, the plate is attached to the antero-lateral portions of at least first and second vertebrae and is structured to facilitate engagement of the plate to the vertebrae from an approach extending in the anterior-posterior directions.

16 Claims, 9 Drawing Sheets

U.S. PATENT DOCUMENTS

| | | |
|---|---|---|
| 5,904,683 A | 5/1999 | Pohndorf et al. |
| 6,017,345 A | 1/2000 | Richelsoph |
| 6,022,350 A | 2/2000 | Ganem |
| 6,120,503 A | 9/2000 | Michelson |
| 6,139,550 A | 10/2000 | Michelson |
| 6,152,927 A | 11/2000 | Farris et al. |
| 6,156,037 A | 12/2000 | LeHuec et al. |
| 6,193,721 B1 | 2/2001 | Michelson |
| 6,224,602 B1 | 5/2001 | Hayes |
| 6,228,085 B1 * | 5/2001 | Theken et al. ............... 606/289 |
| 6,235,034 B1 | 5/2001 | Bray |
| 6,235,059 B1 | 5/2001 | Benezech et al. |
| 6,258,089 B1 | 7/2001 | Campbell et al. |
| 6,261,291 B1 | 7/2001 | Talaber et al. |
| 6,290,703 B1 | 9/2001 | Ganem |
| 6,331,179 B1 | 12/2001 | Freid et al. |
| 6,413,259 B1 | 7/2002 | Lyons et al. |
| 6,565,571 B1 | 5/2003 | Jackowski et al. |
| 6,602,255 B1 | 8/2003 | Campbell et al. |
| 6,652,525 B1 | 11/2003 | Assaker et al. |
| 6,830,571 B2 | 12/2004 | Lenke et al. |
| 6,884,242 B2 | 4/2005 | LeHuec et al. |
| 2002/0022843 A1 | 2/2002 | Michelson |
| 2002/0147450 A1 | 10/2002 | LeHuec et al. |
| 2003/0040746 A1 | 2/2003 | Mitchell et al. |
| 2003/0125739 A1 | 7/2003 | Bagga et al. |
| 2003/0195624 A1 | 10/2003 | Muhanna et al. |
| 2004/0034356 A1 | 2/2004 | LeHuec et al. |
| 2004/0039387 A1 | 2/2004 | Gause et al. |
| 2004/0225290 A1 | 11/2004 | Ferree |
| 2004/0236333 A1 | 11/2004 | Lin |
| 2006/0036250 A1 | 2/2006 | Lange et al. |
| 2006/0241615 A1 | 10/2006 | Melkent |

FOREIGN PATENT DOCUMENTS

| | | |
|---|---|---|
| EP | 0599766 A1 | 6/1994 |
| EP | 0820730 B1 | 1/1998 |
| EP | 0988833 B1 | 10/2003 |
| EP | 1402829 A2 | 3/2004 |
| FR | 2740321 A1 | 4/1997 |
| FR | 2792185 A1 | 10/2000 |
| WO | WO 95/25474 | 9/1995 |
| WO | WO 96/14802 | 5/1996 |
| WO | WO 00/78238 | 12/2000 |
| WO | WO 2006/020456 A1 | 2/2006 |

* cited by examiner

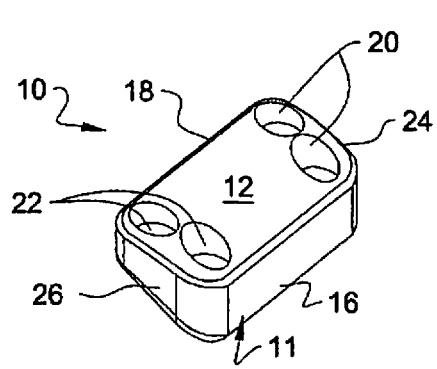
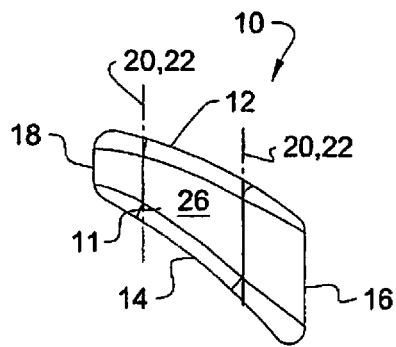
Fig. 1    Fig. 2
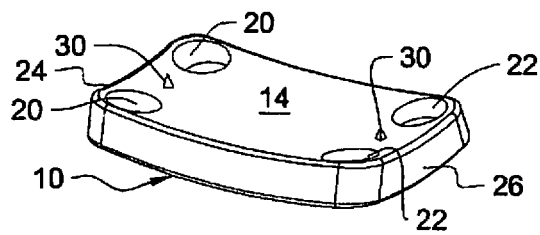
Fig. 3
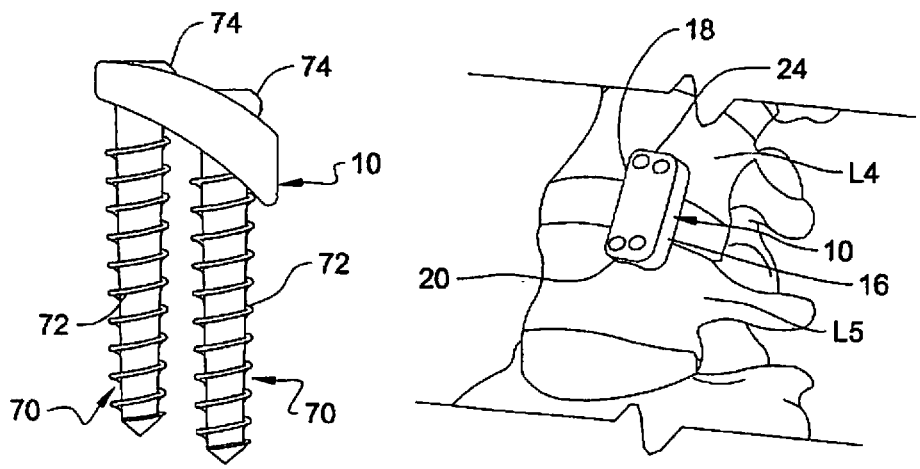
Fig. 4    Fig. 5

ANTERO-LATERAL PLATING SYSTEMS AND METHODS FOR SPINAL STABILIZATION

CROSS-REFERENCE RELATED APPLICATION

The present application is a continuation of U.S. patent application Ser. No. 12/660,223, filed on Feb. 23, 2010, now allowed, which is a continuation of application Ser. No. 11/109,164, filed on Apr. 19, 2005, issued as U.S. Pat. No. 7,678,113. Each of the referenced applications being incorporated by reference herein in their respective entirety.

BACKGROUND

Various types of plating devices and systems have been used to stabilize portions of bones including the spine. Spinal stabilization techniques have employed plating on the posterior, anterior, lateral, postero-lateral and antero-lateral portions of a spinal column segment. Such plating systems can provide fixation of a spinal column segment for the repair of injured or diseased vertebrae, intervertebral discs, and other elements of the spinal column. There remains a need for spinal plating systems that address antero-lateral fixation of the spinal column.

SUMMARY

Antero-lateral plating systems are provided that are securable antero-laterally along two or more vertebrae to provide stabilization.

According to one aspect, a method for securing a plate to at least two vertebrae of a patient includes: accessing the vertebrae from a direct anterior approach; positioning a plate antero-laterally along the at least two vertebrae on a first side of a sagittal plane of the patient, and during the positioning the plate including anchor members adjacent a lateral side of the plate extending from a lower surface thereof; inserting the anchor members into bores formed in the vertebrae to the first side of the sagittal plane; and positioning bone fasteners through holes of the plate adjacent a medial side of the plate along an approach offset to the first side of the sagittal plane to secure the plate to the at least two vertebrae.

According to another aspect, there provided a plating system for stabilization of a spinal column segment. The system comprises a plate having at least a first hole and a second hole therethrough between an upper surface and a lower surface of the plate to receive bone fasteners for passage into first and second vertebrae. The first and second holes are located adjacent a medial side of the plate, and a lower surface of the plate is structured for positioning along an antero-lateral portion of the first and second vertebrae. The first and second holes extend along first and second axes, respectively. The first and second hole axes are non-orthogonally oriented relative to the lower surface of the plate to receive bone fasteners positioned therethrough in a direction parallel to a sagittal plane of the spinal column segment when the plate is positioned along the antero-lateral portion of the first and second vertebrae. The plate further includes first and second anchor members extending from the lower surface at a location between a lateral side of the plate and a respective one of the first and second holes. The anchor members are positionable into the vertebrae as the plate is positioned along the antero-lateral portion of the first and second vertebrae.

According to another aspect, a plating system for stabilization of a spinal column segment is provided. The plating system includes a plate having at least a first hole and a second hole therethrough between an upper surface and a lower surface of the plate to receive bone fasteners for passage into first and second vertebrae. The first and second holes are located adjacent a first side of the plate. The first and second holes extend along first and second axes, respectively, that are non-orthogonally oriented to the lower surface of the plate to receive the bone fasteners positioned therethrough. The plate further includes first and second anchor members secured with the plate and extending from the lower surface at a location between a second side of the plate and a respective one of the first and second holes. The anchor members are generally orthogonally oriented to the lower surface of the plate and extend along an axis intersecting a respective one of the first and second hole axes.

According to a further aspect, a method for securing a plate to at least two vertebrae of a patient includes: accessing first and second vertebrae from a direct anterior approach; forming a first bore in the first vertebra and a second bore in the second vertebra from the direct anterior approach, the first and second bores being offset laterally to a first side of a sagittal plane of the spinal column segment and being angled into the vertebrae in a direction toward the sagittal plane; positioning a plate antero-laterally on the first side of the sagittal plane with anchor members extending from a lower surface of the plate aligned with respective ones of the first and second bores; inserting the anchor members in respective ones of the first and second bores until the lower surface of the plate is positioned on the first and second vertebrae; and engaging the plate to the first and second vertebrae with bone fasteners extending through first and second holes of the plate, the first and second holes being located medially of the first and second anchor members.

These and other aspects are discussed further below.

BRIEF DESCRIPTION OF THE DRAWINGS

FIG. 1 is a perspective view of one embodiment antero-lateral plate.

FIG. 2 is an end view of the plate of FIG. 1.

FIG. 3 is a bottom perspective view of the plate of FIG. 1.

FIG. 4 is an end view of the plate of FIG. 1 with bone engaging fasteners positioned therethrough.

FIG. 5 is a perspective view of a spinal column segment with the plate of FIG. 1 positioned thereon.

DESCRIPTION OF THE ILLUSTRATED EMBODIMENTS

Figure 6:
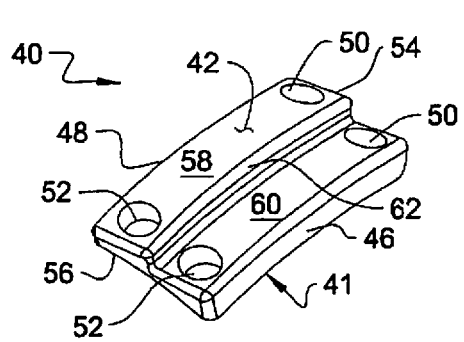
FIG. 6 is a perspective view of another embodiment antero-lateral plate.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

Antero-lateral plates are provided for attachment to a bony segment of the human body, such as two or more vertebrae of the spinal column. In some applications, placement of the plate in antero-lateral position can minimize intrusion or contact of the plate with the great vessels extending anteriorly along the spinal column. The plate is attachable to the antero-lateral or oblique aspect of the two or more vertebrae in an anterior approach to the spine. When in the antero-lateral position the plates are configured to receive bone fasteners from an anterior-posterior trajectory through the anterior approach to minimize intrusion into tissue lateral of the anterior approach. The plate can be employed for antero-lateral spinal stabilization in conjunction with anterior fusion procedures through the same anterior approach created for placement of the fusion construct in a disc space between vertebrae.

It is contemplated that the plates can be attached to any one or combination of the cervical, thoracic, lumbar and sacral regions of the spinal column. The plates can be employed uni-laterally, i.e. a single plate attached to the vertebrae along one side of the midline of the spinal column. The plates can also be employed bi-laterally, i.e. two plates attached to the vertebra on opposite sides of the midline of the spinal column. In either uni-lateral or bi-lateral employment of the plates, multiple plates may be employed to stabilize the same vertebral levels or multiple levels of the spinal column. The plates can also be modular for attachment to one another to form a plate assembly extending along multiple vertebral levels.

The plate can be fixed to each vertebra by at least one bone engaging fastener adjacent each end of the plate. In one specific embodiment, the plate includes a first portion positionable along an upper vertebra, a second portion positionable along a lower vertebra, and a middle portion therebetween extending along the spinal disc space between the adjacent vertebrae. The first portion includes a pair of holes for receiving bone engaging fasteners to engage the plate to the upper vertebra, and the second portion includes a pair of holes for receiving bone engaging fasteners to engage the plate to the lower vertebra. In a further embodiment, the plates includes a third portion having at least one hole for receiving a bone engaging fastener to engage the plate to a third vertebra. In still another embodiment, the plate includes anchor members formed or secured with the plate along a lateral side of the plate. The anchor members are delivered simultaneously with the plate to the implantation location and inserted into respective vertebrae.

The plate may be provided with one or more retaining members that are engageable to or attached to the plate and which resist the bone fasteners from backing out of the plate holes in situ. Examples of such retaining devices are provided in U.S. Pat. Nos. 6,152,927; 6,533,786; 5,364,399, and U.S. patent application Ser. No. 10/219,516; each of which is incorporated herein by reference in its entirety. Other embodiment retaining members are also contemplated, including snap rings positioned in, about or adjacent each of or multiple ones of the plate holes. The snap rings can allow passage, therethrough or thereagainst, of the bone engaging fastener into the plate hole and into the vertebra. A contact surface, a mating receptacle, or other structure formed by the bone engaging fastener aligns with and contacts or receives the snap ring as it returns toward its pre-insertion configuration. Interference between the snap ring and the bone engaging fastener prevents or resists back-out of the bone engaging fastener relative to the plate.

Referring to FIGS. 1-5, there is shown a plate 10 attachable to first and second vertebrae of a spinal column segment. Plate 10 includes a body 11 having an upper surface 12 and an opposite lower surface 14. Body 11 extends between a lateral side 16 and a medial side 18, and also between a cephalad end 24 and a caudal end 26. A pair of first holes 20 are provided adjacent cephalad end 24 and a pair of second holes 22 are provided adjacent caudal end 26.

Holes 20, 22 extend between and open at upper and lower surfaces 12, 14, and are sized to receive a bone fastener therethrough, as shown in FIG. 4. Other embodiments contemplate that only one hole is provided adjacent one or both of the ends 24, 26. Still other embodiments contemplate more than two holes at one or both of the ends 24, 26. Further embodiments contemplate body 11 is sized to extend along three or more vertebrae, and that one or more holes are provided through body 11 at each vertebral level between cephalad end 24 and caudal end 26.

As shown in FIG. 3, one embodiment of plate 10 includes lower surface 14 having spikes 30 projecting therefrom adjacent each of cephalad end 24 and caudal end 26. Spikes 30 can be positioned into respective ones of first and second vertebrae to temporarily secure plate 10 thereto prior to insertion of the bone engaging fasteners. Other embodiments contemplate a plate with more than two spikes 30, one spike 30, or no spikes 30. Still other embodiments contemplate a plate having spikes with no holes for receiving bone engaging fasteners. The spike can engage the plate to the vertebrae, and/or the plate can be coupled to one or both of an intradiscal and extradiscal stabilization construct to secure it to the spinal column segment.

Lower surface 14 can include a concave curvature between lateral side 16 and medial side 18 adapted to conform to the antero-lateral curvature of the vertebral bodies against which plate 10 is to be positioned. Upper surface 12 includes a convex curvature between lateral side 16 and medial side 18. In the illustrated embodiment, the thickness of body 11 is greater at lateral side 16 than at medial side 18. As shown in FIG. 5, this allows lateral side 16 of plate 11 to extend laterally around the vertebral bodies along lower surface 14, while minimizing the intrusion of upper surface 12 of body 11 into the surrounding tissue anteriorly of body 11 and laterally of lateral side 16.

As shown in FIG. 2, holes 20, 22 extend along axes that are non-orthogonal to lower surface 14. In this configuration, the axes of holes 22, 24 are oriented so that their axes extend in the anterior-posterior direction which is generally parallel to the sagittal plane when plate 10 is position in an antero-lateral location along the vertebrae, as shown in FIG. 5. Bone engaging fasteners 70 are shown in FIG. 4, and are positionable through holes 20, 22 to the respective vertebrae of the spinal column segment. In the illustrated embodiment, bone engaging fasteners 70 include a threaded shaft 72 projecting below lower surface 14 for engaging with the underlying bony structure. Bone engaging fasteners 70 further include an enlarged head 74 residing in respective ones of the holes 20, 22 adjacent upper surface 12. Enlarged head 74 contacts body 11 and secures plate 10 against the bony structure when head 74 is positioned against body 11.

Figure 10:
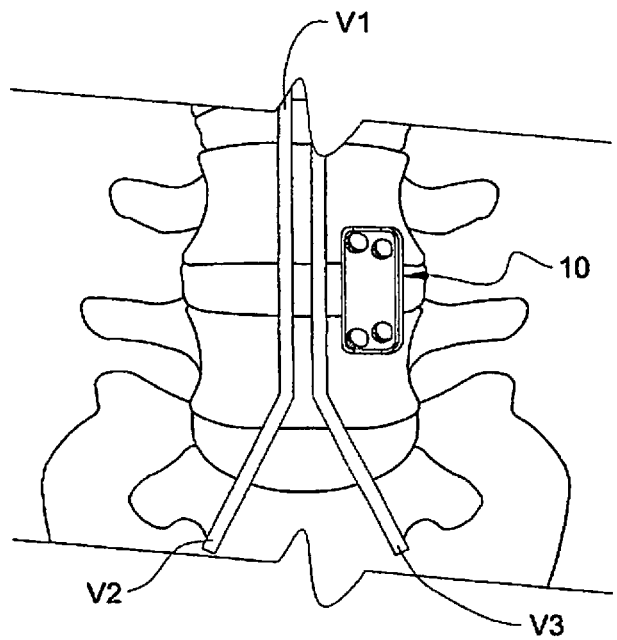
FIG. 10 is an elevational view of the spinal column segment with the plate of FIG. 1 engaged thereto along one antero-lateral side of the spinal column segment.
Figures 16, 17:
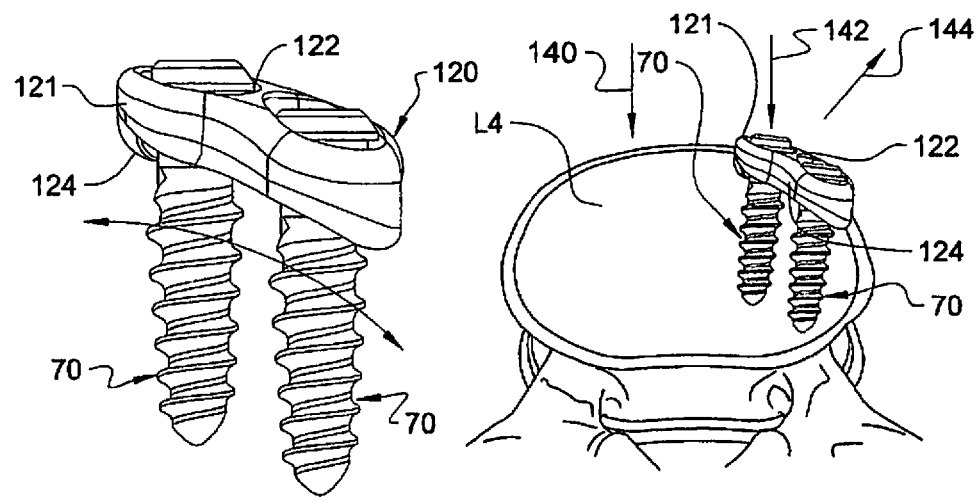
FIG. 16 is an end elevation view of the plate of FIG. 12 with bone engaging fasteners positioned therethrough.
FIG. 17 is an end elevation view showing the plate engaged antero-laterally to a vertebral body.
Figure 18:
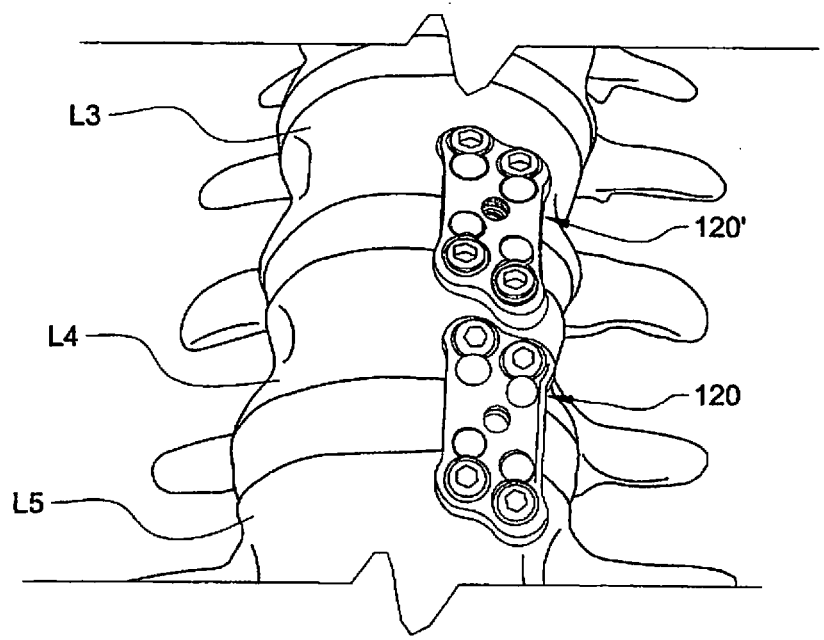
FIG. 18 is a plan view showing plates engaged antero-laterally along multiple vertebral levels.

As shown in FIG. 5 and also at least in FIGS. 10, 17 and 18 for the other plate embodiments, one embodiment of the implanted orientation for plate 10 contemplates antero-lateral positioning along the L4 and L5 vertebrae. Cephalad end 24 is located along vertebra L4, and caudal end 26 is located along vertebra L5. Medial side 18 is oriented medially or toward the spinal mid-line, and lateral side 16 is oriented laterally or away from the spinal mid-line. Plate 10 is positioned, relative to the patient, on the left hand side of the spinal mid-line. Other embodiments contemplate a mirror image of plate 10 for placement on the right hand side of the spinal midline.

In its implanted orientation, plate 10 is located laterally of the great vessels V1 extending along the spinal midline. In the illustrated embodiment, placement of the plate on the L4-L5 vertebrae locates the plate cephaladly of the bifurcation V2, V3 of the great vessels V1. The intrusiveness of the procedure is minimized since plate 10 avoids contact with the great vessels along the anterior side of the spinal column. Plate 10 can be positioned along the spinal column through the same approach taken for access to the disc space between the IA and L5 vertebrae for placement of a fusion construct. The invasiveness of the procedure is minimized since external stabilization can be provided without a posterior intrusion for placement of a plate or rod construct. Also, alignment of the axes of holes 20, 22 in the portal formed by the anterior approach minimizes intrusion laterally into tissue along the approach during placement of the bone fasteners through the plate holes.

Figure 7:
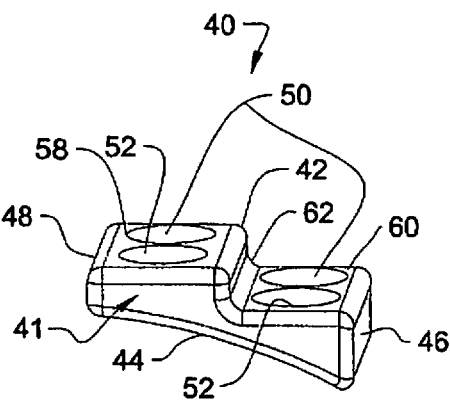
FIG. 7 is an end perspective view of the plate of FIG. 6.
Figure 8:
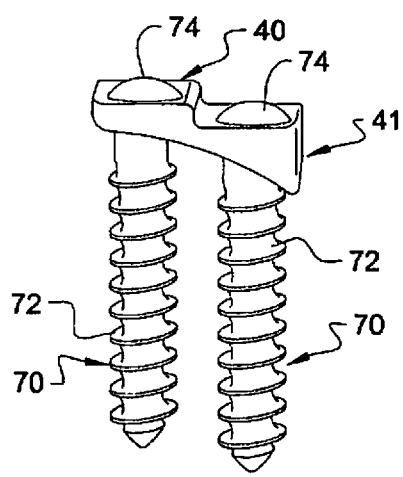
FIG. 8 is an end view of the plate of FIG. 6 with bone engaging fasteners positioned therethrough.

Another embodiment plate 40 is shown in FIGS. 6-9. Plate 40 attachable to first and second vertebrae of a spinal column segment, such as vertebrae L4 and L5 shown in FIG. 9. Plate 40 includes a body 41 having an upper surface 42 and an opposite lower surface 44. Body 41 extends between a lateral side 46 and a medial side 48, and also between a cephalad end 54 and a caudal end 56. A pair of first holes 50 are provided adjacent cephalad end 54 and a pair of second holes 52 are provided adjacent caudal end 56. Holes 50, 52 extend between and open at upper and lower surfaces 42, 44, and are sized to receive a bone engaging fastener therethrough, as shown in FIG. 8.

Other embodiments contemplate that one hole is provided adjacent one or both of the ends 54, 56. Still other embodiments contemplate more than two holes at one or both of the ends 54, 56. Further embodiments contemplate body 41 is sized to extend along three or more vertebrae, and that one or more holes are provided through body 41 at each vertebral level between cephalad end 54 and caudal end 56.

Figure 9:
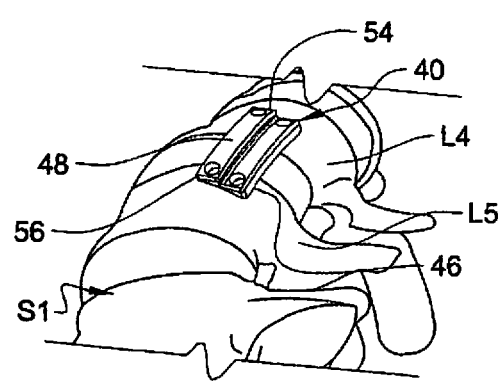
FIG. 9 is a perspective view of the spinal column segment with the plate of FIG. 6 positioned thereon.

Lower surface 44 can include a concave curvature between lateral side 46 and medial side 48 adapted to conform to the antero-lateral curvature of the vertebral bodies against which plate 40 is to be positioned. Upper surface 42 includes a first portion 58 adjacent medial side 48 and a second portion 60 adjacent lateral side 46. A riser portion 62 extends between first and second portions 58, 60. Upper surface 42 thus forms a stair-stepped configuration extending between the medial and lateral sides 48, 46. In the illustrated embodiment, the thickness of body 41 is greater at lateral side 46 than at medial side 48. As shown in FIG. 9, this allows lateral side 46 of body 41 to extend laterally around the vertebral bodies along lower surface 44, while minimizing the intrusion of upper surface 42 of body 41 into the surrounding tissue located anteriorly of body 41 and laterally of lateral side 46.

As shown in FIG. 7, holes 50, 52 extend along axes that are non-orthogonal to lower surface 44, but orthogonally oriented to the portion of upper surface 42 extending along respective ones of the first and second portions 58, 60. In this configuration, holes 50, 52 are oriented so that their axes extend in the anterior-posterior directions and generally parallel with the sagittal plane when plate 10 is position in an antero-lateral location along the vertebrae, as shown in FIG. 9. Bone engaging fasteners 70 are shown in FIG. 8, and are positionable through holes 50, 52 to engage plate 40 to the respective vertebrae of the spinal column segment. Upper surface portions 58, 60 extend generally parallel to one another, and can act as a guide for placement of bone engaging fasteners 70 through the holes 50, 52.

Figure 11:
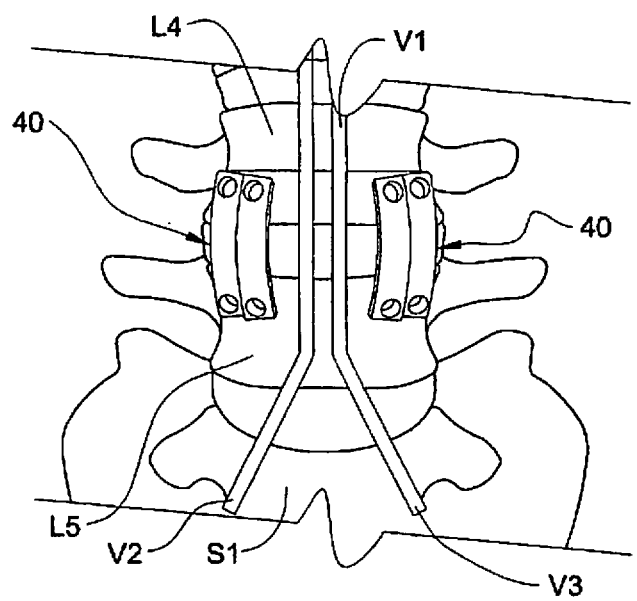
FIG. 11 is an elevational view of the spinal column segment with plates of FIG. 6 positioned along each antero-lateral side of the spinal column segment.

As shown in FIG. 9 and also in FIG. 11, one embodiment of the implanted orientation for plate 40 contemplates antero-lateral positioning along the L4 and L5 vertebrae. Cephalad end 54 is located along vertebra L4, and caudal end 56 is located along vertebra L5. Medial side 48 is oriented medially or toward the spinal mid-line, and lateral side 46 is oriented laterally or away from the spinal mid-line. In FIG. 9, one plate 40 is positioned, relative to the patient, on the left hand side of the spinal mid-line. Other embodiments contemplate a mirror image of plate 40 for placement on the right hand side of the spinal midline, such as shown in FIG. 11, to provide bi-lateral extradsical stabilization of the vertebral level.

Similar to plate 10, in its implanted orientation plate 40 is located laterally of the great vessels V1 extending along the spinal midline. In the illustrated embodiment, placement of the plate on the L4-L5 vertebrae locates the plate cephaladly of the bifurcation V2, V3 of the great vessels V1. The intrusiveness of the procedure is minimized since plate 40 avoids contact with the great vessels along the anterior side of the spinal column. Plate 10 can be positioned along the spinal column through the same portal forming the anterior approach taken for access to the disc space between the L4 and L5 vertebrae for placement of a fusion construct. The invasiveness of the procedure is minimized since external stabilization can be provided without posterior intrusion for placement of a plate or rod construct. Also, alignment of the axes of holes 50, 52 generally parallel with the sagittal plane in the portal of the anterior approach minimizes intrusion laterally into tissue along the approach for placement of the bone fasteners through the plate holes.

Figure 12:
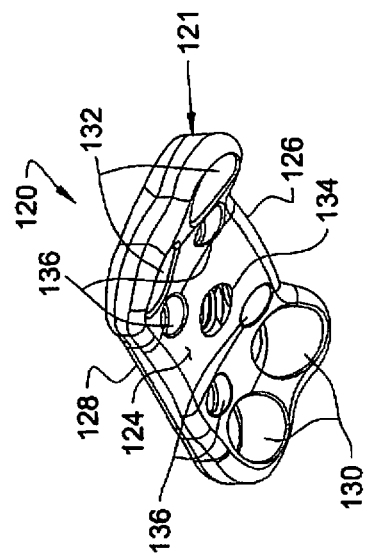
FIG. 12 is a perspective view looking toward the upper surface of another embodiment antero-lateral plate.
Figure 13:
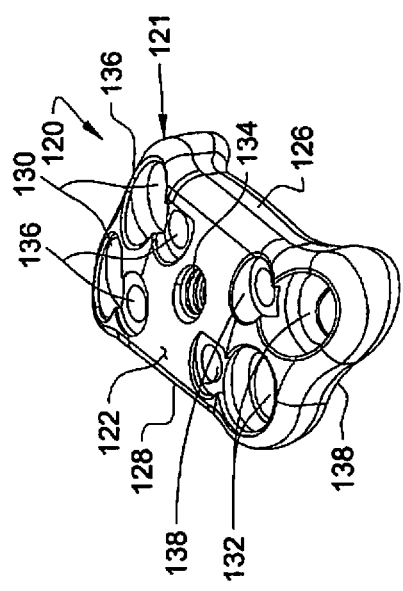
FIG. 13 is a perspective view looking toward the lower surface of the plate of FIG. 12.

Referring now to FIGS. 12-13, there is shown another embodiment plate 120 for antero-lateral stabilization of a spinal column segment. Plate 120 includes a body 121 having an upper surface 122 and an opposite lower surface 124. Body 121 extends between a lateral side 126 and a medial side 128, and also between a cephalad end 136 and a caudal end 138. A pair of first holes 130 are provided adjacent cephalad end 136 and a pair of second holes 132 are provided adjacent caudal end 138. Holes 130, 132 extend between and open at upper and lower surfaces 122, 124, and are sized to receive a bone engaging fastener therethrough, as shown in FIGS. 16-17. The corners of plate 120 about holes 130, 132 and the transitions between adjacent plate surfaces can be smooth and rounded to eliminate sharp or abrupt corners or transitions that might impinge on adjacent tissue and anatomical structures.

Plate 120 is further shown with first bores 136 adjacent respective ones of the first holes 130 and second bores 138 adjacent respective ones of the second holes 132. First and second bores 136, 138 can receive retaining mechanisms to secure and/or prevent the bone engaging fasteners from backing out of the plate holes. Such retaining mechanisms may include set screws, snap rings, screw and washer combinations, or any other retaining mechanism embodiment. There is further provided a central bore 134 that can be engaged with an inserter, drill guide or other instrument to facilitate placement and securement of plate 120 along the spinal column. In still a further embodiment, a fastener can be engaged to central bore 134 to secure a retaining member on upper surface 122 of plate 120. In still another embodiment, central bore 134 can include one or more bores for receiving one or more fasteners to engage an interbody device or a vertebral body through plate 120. Other embodiments of plate 120 contemplate that any or all of the bores 134, 136, 138 are not provided.

Figure 14:
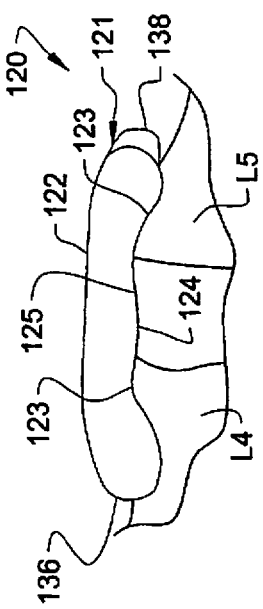
FIG. 14 is a medial-lateral section view through the plate of FIG. 12.

As shown in FIGS. 14, 16 and 17, lower surface 124 can include a concave curvature between lateral side 126 and medial side 128 adapted to conform to the antero-lateral curvature of the vertebral bodies against which plate 120 is to be positioned. Upper surface 122 includes a convex curvature between lateral side 126 and medial side 128. In the illustrated embodiment, the thickness of body 121 is greater at lateral side 126 than at medial side 128. As discussed above with respect to other plate embodiments, this allows lateral side 126 of plate 120 to extend laterally around the vertebral bodies along lower surface 124, while minimizing the intrusion of upper surface 122 of body 121 into the surrounding tissue toward medial side 128.

Figure 15:
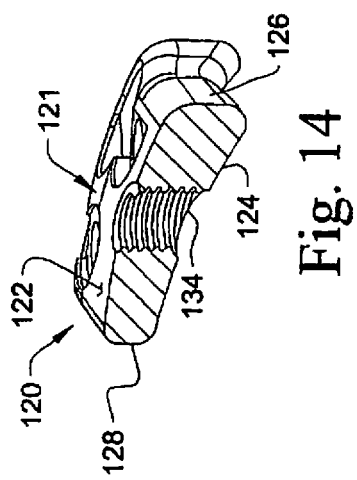
FIG. 15 is an elevation view of the plate of FIG. 12 positioned along a vertebral level of the spinal column.

As shown in FIG. 15, lower surface 124 of plate 120 can also be curved to conform to the vertebral surface profile in the cephalad and caudal directions. For example, body 121 may include a convexly curved discal portion 125 positionable extradiscally along the intervertebral disc between vertebrae, and concavely curved pockets 123 at each end of portion 125 to receive the cortical rim of the respective adjacent vertebra. The portions of lower surface 122 extending along cephalad and caudal ends 136, 138 are each angled to slope away from upper surface 122 and in the same direction relative to the adjacent discal portion 125 to conform to the outer surface profile of the adjacent vertebral bodies. The cephalad-caudal curvature in combination with the medial-lateral curvature of body 121 forms a low profile footprint projecting outwardly from the vertebral bodies.

As shown in FIGS. 16-17, one embodiment of plate 120 includes lower surface 124 curved to conform to the antero-lateral profile of the vertebrae in the medial-lateral direction. As discussed above with respect to the other plate embodiments, such curvature facilitates placement of plate 120 along an anterior-posterior placement axis 142 in an anterior approach 140 to the spinal column segment. The axes of holes 130, 132 also extend in a direction parallel to anterior placement axis 142, which is also parallel to the sagittal plane. The axes of holes 130, 132 are obliquely oriented relative to lower surface 124 of plate 120. In the operative position, the axes of holes 130, 132 are also obliquely oriented relative to a normal axis 144, which is also normal to the vertebral surfaces along which lower surface 124 is placed.

Referring now to FIG. 18, there is shown a multi-level stabilization placement of plates 120 along multiple levels of the spinal column. The cephalad ends of each of the plates 120, 120' include staggered profiles so that the medial side of each plate extends more cephaladly than the lateral side. The caudal ends of each of the plates 120, 120' include a staggered profile so that the lateral side extends more caudally than the medial side. The cephalad and caudal ends of the plates 120, 120' also include concavely curved or recessed end wall portions between the plate holes to nestingly receive a respective node or projecting portion of the other plate member, guiding the positioning of the plates relative to one another and allowing placement of the plates closely to one another.

Figure 19:
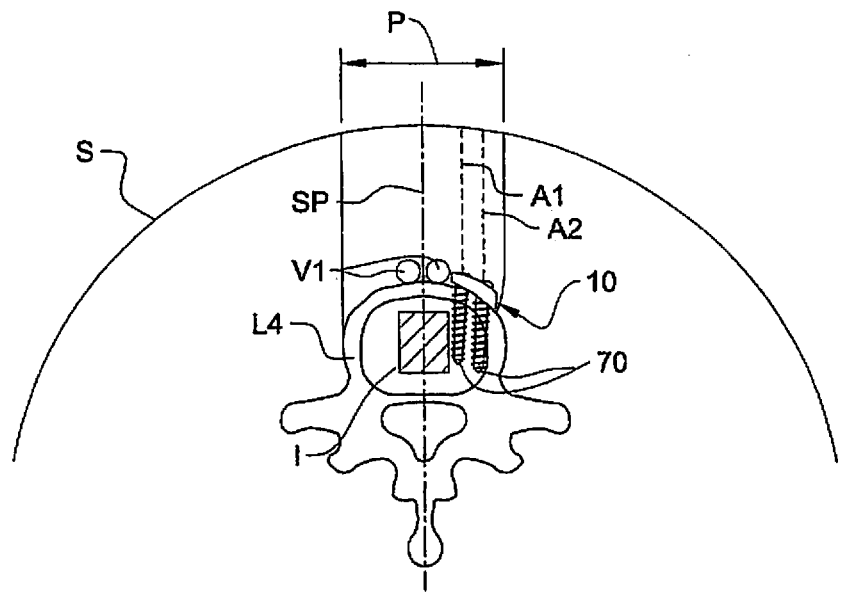
FIG. 19 is a view looking along the spinal midline showing an anterior surgical approach for engaging an antero-lateral plate to the spinal column.

Referring now to FIG. 19, a procedure with plate 10 will be describe, it being understood that the procedure also has application with the other plate embodiments discussed herein. An anterior incision is made in skin S of the patient and an access portal P is formed to access one or more vertebral levels including vertebra LA, it being understood that access to other vertebral levels not including vertebra L4 is also contemplated. Access portal P provides a direct anterior approach to the spinal column that is generally centered about the sagittal plane SP. Great vessels V1 are manipulated with a retractor or other instrument for accessing a spinal disc space for preparation of the disc space and vertebra to receive a fusion construct I. Fusion construct I may include any one or more of a threaded fusion cage, a push-in cage, a bone implant, a spacer, bone graft; and bone growth material and therapeutic substances. Fusion construct I can be symmetrical or asymmetrical relative to sagittal plane SP. Placement of fusion construct I can be guided or facilitated with guide sleeves, retractors, ramps, inserters, or any other device or instrument for placement of the same. It is further contemplated that fusion constructs can be employed at multiple levels along the spinal column.

With fusion construct I in the disc space between vertebrae, plate 10 can be positioned along the antero-lateral aspect of the vertebrae between which the fusion construct is positioned. Lower surface 14 is shaped to conform to this antero-lateral profile, while upper surface 12 is oriented toward and accessible in portal P. In some procedures, the soft tissues along portal P can be shifted laterally to provide additional space for placement of and access to plate 10.

Bone fasteners 70 are then positioned through plate holes 20, 22 to secure plate 10 to the vertebrae. Bone fasteners 70 can be positioned along approach axes A1 and A2 extending from holes 20, 22. Approach axes A1, A2 extend generally parallel to sagittal plane SP, thus allowing the bone fasteners to be engaged to the vertebrae without additional retraction or displacement of tissue to accommodate placement of bone fasteners 70. A standard straight driver instrument can be employed through portal P to engage the bone fasteners 70 to the vertebrae. If bi-lateral stabilization is desired, a second plate can be engaged antero-laterally to the vertebrae on the opposite side of sagittal plane SP. The plate embodiments discussed herein provide for antero-lateral stabilization with plate and fastener placement through the same direct anterior approach employed for an anterior interbody fusion procedure.

The plate embodiments discussed herein can include cephalad and caudal ends that are angled toward one another toward the medial side of the plate to limit the medial dimension of the plate and also to allow placement of the plate holes closer to the central axis of the plate, minimizing the width of the plate. The corners of the plate body transitioning between the sides and ends of the plate body can be rounded to eliminate sharp or abrupt edges that could pinch, cut or wear against tissue. The surfaces of the plate body transitioning between the upper and lower surfaces can also be smooth and rounded to eliminate sharp or abrupt edges that could pinch, cut or wear against tissue.

It is contemplated that the overall configuration of the plates can be standardized and provided in a range of sizes. The external dimensions of the plate can also vary depending on the patient anatomy determined according to standardized measurements or pre-operative modeling of the region to be stabilized. The plates can have a shape suited for antero-lateral attachment to vertebrae of a spinal column segment in the cervical, thoracic, lumbar and sacral regions.

The plate holes and fasteners can be configured such that the fasteners have a fixed angle orientation relative to the plate or variable angle orientations. One or more of the holes can be circular, or elongated to allow translation of the fastener along the hole. The holes can include a recessed surface extending thereabout that allows the head of the bone fastener to be recessed into the plate, minimizing extension of the fastener from the plate into the tissue adjacent the plate. One or more retaining members may be employed with the plate to prevent the fasteners from backing out of the plate holes, to engage the fasteners in the plate holes, and/or to fix the fasteners in the plate holes.

Figure 20:
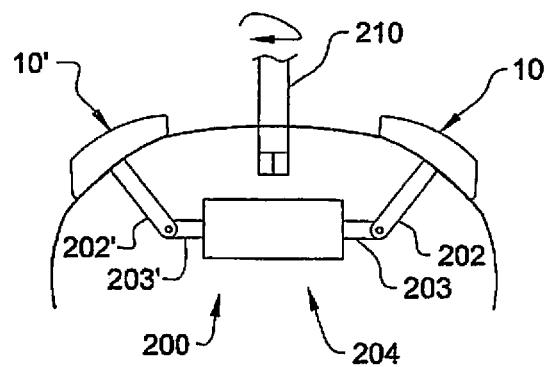
FIG. 20 is an end view of two plates positioned along a vertebral body and an intradiscal coupling mechanism interconnecting the plates.

Referring now to FIG. 20, there is shown another embodiment procedure where a first plate 10 is positioned antero-laterally along one side of the spinal column and a second plate 10' is positioned antero-laterally along another side of the spinal column. The bi-lateral, antero-laterally positioned plates are connected to one another through an intradiscal coupling mechanism 204. Coupling mechanism 204 can be an interbody device, connector bar, or fusion construct in the disc space that extends between the plates.

To accommodate variability of the anatomy of the spinal column segment and the spacing between plates, in one embodiment the coupling mechanism includes a connector bar that is length adjustable. In a further embodiment, the connector bar includes flexible or hinged connections to the plates to allow adjustment in the relative orientation between the connector bar and the plates. In still another embodiment, the coupling mechanism is a turnbuckle, center screw, or a slider-lever, for example.

In one specific embodiment, the connector bar includes a spinning connector piece that interconnects links 203, 203'. The spinning piece can be mounted to and freely rotatable to one of the links 203, 203', and threadingly engaged to the other of the links 203, 203'. Rotation of the spinning piece shortens or lengthens coupling mechanism 204 between plates 10, 10'.

Still further it is contemplated that plates 10, 10' may include connecting arms 202, 202' pivotally and/or slidably connected to coupling mechanism 204. The arms 202, 202' pivot relative to coupling mechanism 204 as it is shortened or lengthened. As coupling mechanism 204 is shortened, plates 10, 10' are drawn toward and into firm engagement with the adjacent antero-lateral vertebral surfaces. The pivotal connections can be provided by a ball joint, universal joint, pinned joint, or other suitable connector. The connector can be lockable to secure connecting arms, 202, 202', links 203, 203' and/or coupling mechanism 204 in a desired relative orientation with plates 10, 10'.

Figure 21:
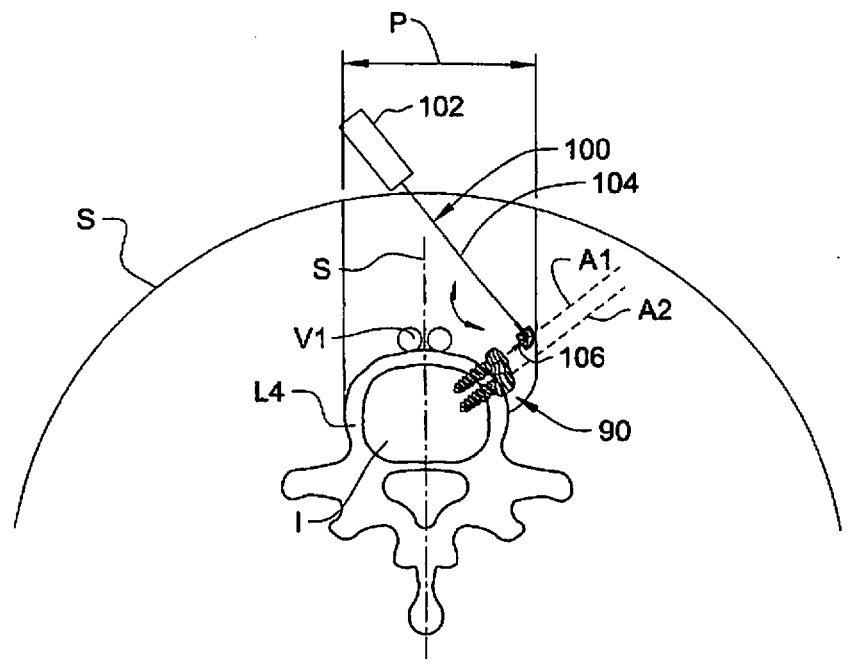
FIG. 21 is a view looking along the spinal midline showing an instrument and technique for engaging another antero-lateral plate embodiment to the spinal column.
Figure 22:
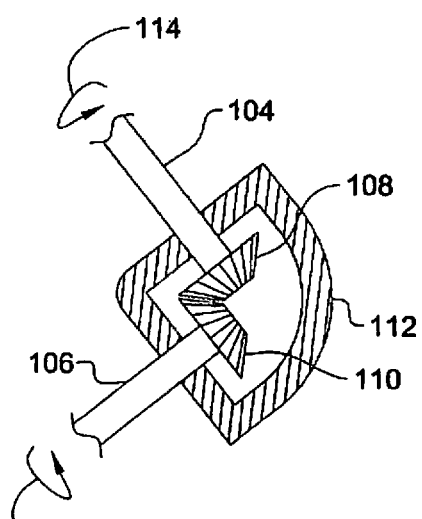
FIG. 22 is an elevation view in partial-section showing a portion of the instrument of FIG. 21.

Referring now to FIGS. 21 and 22, there is shown another embodiment procedure for placement and engagement of a plate 90 antero-laterally along two or more vertebrae in conjunction with direct anterior placement of a fusion construct in one or more disc spaces between vertebrae. Plate 90 includes fasteners 70 extending therethrough along axes A1, A2 that are orthogonal to the lower surface of plate 90 and obliquely oriented to the sagittal plane. Accordingly, when plate 90 is positioned antero-laterally as shown in FIG. 13, the hole axes A1, A2 project outside the portal P forming the direct anterior approach to the vertebrae.

An instrument 100 is provided that is structured to engage bone fasteners 70 in the holes of plate 100 while instrument 100 is positioned in portal P. Instrument 100 includes a handle 102, a first shaft portion 104, and a second shaft portion 106 angularly and rotatably coupled to first shaft portion 104. As shown in FIG. 22, one embodiment connection mechanism between shaft portions 104, 106 include a beveled gear 108 at a distal end of first shaft portion 104, and second shaft portion 106 includes a beveled gear 110 at a proximal end thereof. Gears 108, 110 can be received in housing 112 to prevent pinching or wearing of the gears against tissue or other anatomical structures during rotation.

Gears 108, 110 interact with one another so that rotation of first shaft portion 104 in the direction indicated by arrow 112 effects rotation of second shaft portion 106 in the direction indicated by arrow 116. The distal end of second shaft portion 106 can be mounted to the bone fastener extending through a hole in plate 90 and threadingly advances the bone fastener into the plate holes as it is rotated. It is further contemplated that the distal shaft portion 106 can be provided with a modular configuration that accepts attachments for various procedures that may be performed with instrument 100. Such modular tips may include drill, tap, awl, or screwdriver attachments, for example.

In one procedure, instrument 100 is employed to form antero-laterally oriented holes in the vertebrae to receive bone fasteners or anchor members extending from the plate. The holes can be formed to extend along axes A1 and/or A2, for example. The retraction necessary to accommodate insertion of the instrument is minimized by the angled instrument portions since the proximal end of the instrument extends through the direct anterior approach formed by portal P rather than along an extension of the respective axes A1 and/or A2.

Figure 23:
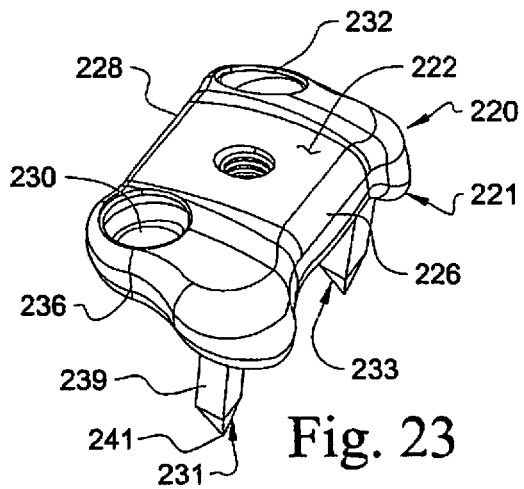
FIG. 23 is a perspective view looking toward the top of another embodiment antero-lateral plate.
Figure 24:
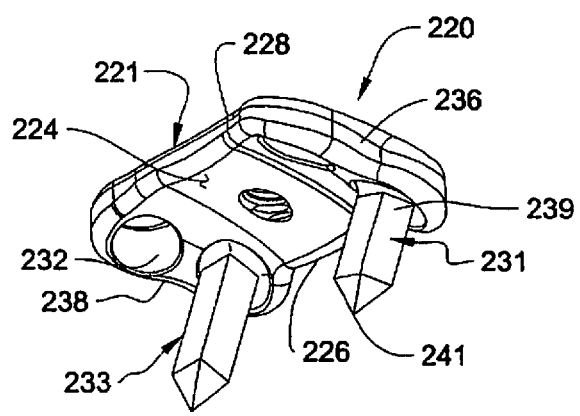
FIG. 24 is a perspective view looking toward the bottom of the plate of FIG. 23.
Figure 25:
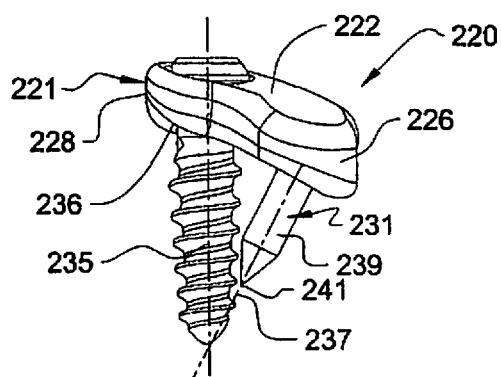
FIG. 25 is a perspective view looking toward the end of the plate of FIG. 23 and a bone engaging fastener positioned through the plate hole.

Referring now to FIGS. 23-25, there is shown another embodiment plate 220 for antero-lateral stabilization of a spinal column segment. Plate 220 includes a body 221 having an upper surface 222 and an opposite lower surface 224. Body 221 extends between a lateral side 226 and a medial side 228, and also between a cephalad end 236 and a caudal end 238. A first hole 230 is provided adjacent cephalad end 236 and a second hole 232 is provided adjacent caudal end 238. Holes 230, 232 extend between and open at upper and lower surfaces 222, 224, and are sized to receive a bone engaging fastener therethrough, as shown in FIG. 25. Holes 230, 232 are located adjacent medial side 228.

Plate 220 further includes anchor members 231, 233 extending from lower surface 224. Anchor members 231, 233 are adjacent lateral side 226. Anchor members 231, 233 can be integrally formed with or engaged to plate 220 prior to implantation of plate 220. The anchor members 231, 233 are secured to plate 220 so that anchor members 231, 233 are delivered to the implantation location as plate 220 is positioned into the patient through the access portal.

In the illustrated embodiment, anchor members 231, 233 each include an elongate body 239 and a distal pointed end 241. Body 239 extends along an axis 237, and includes a polygonal cross-sectional shape transversely to axis 237. In the illustrated embodiment, the cross-sectional shape is a square, and distal end 241 includes a distally oriented pyramidal shape along axis 237. Other embodiments contemplate other cross-sectional shapes for body 239, including rectangular, circular, and non-uniform shapes, for example. The anchor members can include bars, gulls, wings, teeth or other structure along their length to enhance engagement with the bony tissue of the vertebrae and resist pull-out. Anchor members 231, 233 are sized and shaped to secure plate 220 to the vertebra into which anchor members 231, 233 are received, and to maintain the positioning of plate 220 until placement of the bone fasteners through the plate holes 230, 232.

The corners of plate 220 about holes 230, 232 and the transitions between adjacent plate surfaces can be smooth and rounded to eliminate sharp or abrupt corners or transitions that might impinge on adjacent tissue and anatomical structures. Plate 220 is further shown with a central bore 234 that can be engaged with an inserter, drill guide or other instrument to facilitate placement and securement of plate 220 along the spinal column. In still a further embodiment, a fastener can be engaged to central bore 234 to secure a retaining member on upper surface 222 of plate 220. In still another embodiment, central bore 234 can include one or more bores for receiving one or more fasteners to engage an interbody device or a vertebral body through plate 220. Other embodiments of plate 220 contemplate that bore 234 is not provided, or that additional bores or recesses are provided to receiver retaining mechanisms.

Lower surface 224 can include a concave curvature between lateral side 226 and medial side 228 adapted to conform to the antero-lateral curvature of the vertebral bodies against which plate 220 is to be positioned. Upper surface 222 includes a convex curvature between lateral side 226 and medial side 228. In the illustrated embodiment, the thickness of body 221 is greater at lateral side 226 than at medial side 228. As discussed above with respect to other plate embodiments, this allows lateral side 226 of plate 220 to extend laterally around the vertebral bodies along lower surface 224, while minimizing the intrusion of upper surface 222 of body 221 into the surrounding tissue toward medial side 228. Other embodiments contemplate that the lateral side 226 has the same thickness or is less thick than the medial side 228.

Lower surface 224 of plate 220 can also be curved to conform to the vertebral surface profile in the cephalad and caudal directions. For example, body 221 may include a convexly curved discal portion positionable extradiscally along the intervertebral disc between vertebrae, and concavely curved pockets at each end of the discal portion to receive the cortical rim of the respective adjacent vertebrae as discussed above with respect to plate 120. The portions of lower surface 224 extending along cephalad and caudal ends 236, 238 are each angled to slope away from upper surface 222 to conform to the outer surface profile of the adjacent vertebral bodies. The cephalad-caudal curvature in combination with the medial-lateral curvature of body 221 forms a low profile footprint projecting outwardly from the vertebral bodies.

Figure 28:
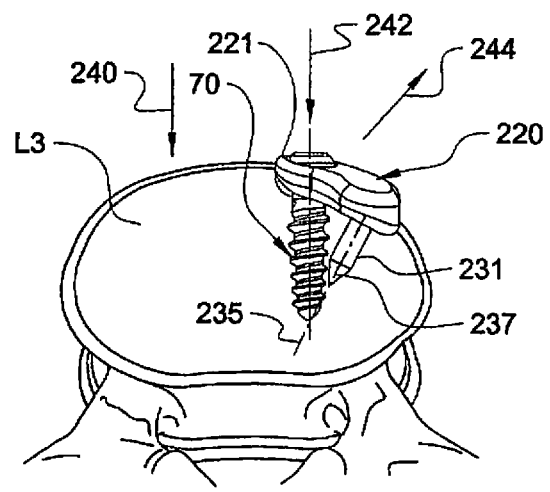
FIG. 28 is an elevation view showing the plate of FIG. 23 engaged to the spinal column segment.

Plate 220 includes lower surface 224 curved to conform to the antero-lateral profile of the vertebrae in the medial-lateral direction. As discussed above with respect to the other plate embodiments, such curvature facilitates placement of plate 220 along an anterior-posterior placement axis 242 in an anterior approach 240 to the spinal column segment, as shown in FIG. 28. The axes 235 of holes 230, 232 extend in a direction generally parallel to anterior placement axis 242, which is also parallel to the sagittal plane. The axes of holes 230, 232 are obliquely oriented relative to lower surface 224 of plate 220. In the implantation orientation of plate 220, the axes of holes 230, 232 are also obliquely oriented relative to a normal axis 244, which axis 244 is also normal to the vertebral surfaces along which lower surface 224 of plate 220 is placed. Anchor members 231, 233 extend along an axis 237 which can be orthogonally oriented to lower surface 224. In the implantation orientation, axis 237 extends into the vertebral body transversely to the sagittal plane and intersects axis 235. The orientations of the fasteners and anchor members indicated by the intersecting axis 235, 237 provide a triangular arrangement by the vertebral body engaging members. This creates a wedge effect to resist displacement of the plate relative to the vertebrae and securely engage plate 220 to the vertebrae.

Figure 26:
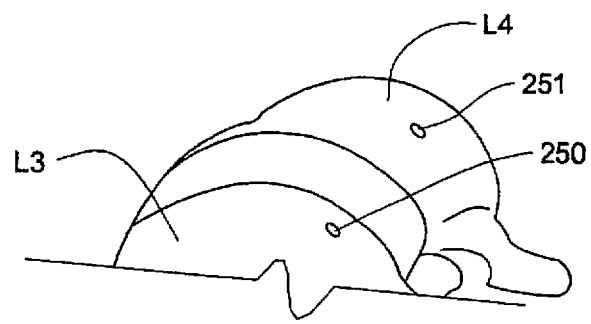
FIG. 26 is a perspective view of a spinal column segment with hole formed for receiving anchoring members of the plate of FIG. 23.
Figure 27:
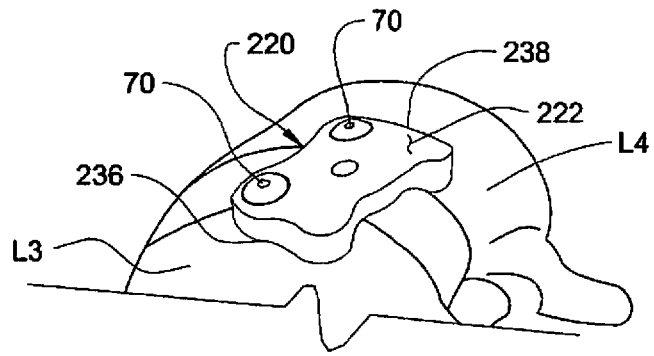
FIG. 27 is a perspective view of the spinal column segment with the plate engaged thereto.

Anchor members 231, 233 are secured with plate 220 so that the anchor members can be positioned in engagement with the vertebrae as plate 220 is positioned along the vertebrae. In one procedure, lateral holes 250, 251 can be formed in vertebrae L3, L4 respectively, as shown in FIG. 26. Such hole formation can be completed from a direct anterior approach utilizing an instrument and awl, such as discussed above with respect to instrument 100. Plate 100 can then be delivered through the direct anterior approach so that anchor members 231, 233 can be positioned into the holes 250, 251. Holes 230, 232 are offset medially toward the sagittal plane of the vertebrae, as shown in FIG. 27. Bone fasteners 70 can then be positioned through holes 230, 232 to secure the plate 220 to vertebrae L3, L4, and drive anchor members 231, 233 further into vertebrae L3, L4 as the bone fasteners are tightened. Although only vertebrae L3, L4 are shown in FIGS. 26-28, it should be understood that plate 220 can be positioned along any portion of the spinal column.

Since the laterally oriented anchor members are pre-attached or integrally formed with plate 220, laterally oriented fasteners need not be positioned through plate 220. This allows plate 220 to be positioned antero-laterally from a direct anterior approach while minimizing or eliminate tissue retraction that would be necessary to install fasteners in any lateral holes of plate 220 in an approach extending along normal axis 244.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A plating system for stabilization of a spinal column segment, comprising:
   a plate having at least a first hole therethrough between an upper surface and a lower surface of said plate to receive a bone fastener for passage into a first vertebra and at least a second hole therethrough between said upper surface and said lower surface of said plate to receive a bone fastener for passage into a second vertebra, said first and second holes being located adjacent a medial side of said plate, wherein said lower surface of said plate is structured for positioning along an antero-lateral portion of the first and second vertebrae, and said first and second holes axes being non-orthogonally oriented relative to said lower surface of said plate to receive said bone fasteners positioned therethrough in a direction generally parallel to a sagittal plane of the spinal column segment when said plate is positioned along the antero-lateral portion of the first and second vertebrae, said plate further including an anchor member adjacent said first opening and an anchor member adjacent said second opening, said anchor members extending from said lower surface along an axis that is orthogonally oriented relative to said lower surface, said anchor members being structured for positioning into the first and second vertebrae as said plate is positioned along the antero-lateral portion of the first and second vertebrae, said anchor members being attached to said plate before fasteners are inserted through said first and second holes.

2. The system of claim 1, wherein said bone fasteners extend into the vertebrae in a direction generally parallel to the sagittal plane when positioned through said plate holes.

3. The system of claim 1, wherein said anchor members each include an elongated body and a pointed distal end.

4. The system of claim 3, wherein said elongated body includes a polygonal cross-sectional shape.

5. The system of claim 4, wherein said polygonal cross-sectional shape is a square and said pointed distal end is pyramidal in shape.

6. The system of claim 1, wherein said plate includes a first thickness between said upper and lower surfaces along said lateral side thereof that is greater than a second thickness between said upper and lower surfaces along said medial side thereof.

7. The system of claim 1, wherein said lower surface of said plate is concavely curved between said medial and lateral sides and said upper surface of said plate is convexly curved between said medial and lateral sides.

8. The system of claim 1, further comprising a first bone fastener positioned in said first hole and a second bone fastener positioned in said second hole, said first and second bone fasteners each extending from a head to a distal tip, said anchor members each extending from a head to a distal tip, said distal tip of said first bone fastener being positioned adjacent said distal tip of one of said anchor members and said distal tip of said second bone fastener being positioned adjacent said distal tip of the other of said anchor members.

9. A plating system for stabilization of a spinal column segment, comprising:

a plate having at least a first hole therethrough between an upper surface and a lower surface of said plate to receive a bone fastener for passage into a first vertebra and at least a second hole therethrough between said upper surface and said lower surface of said plate to receive a bone fastener for passage into a second vertebra, said first and second holes being located adjacent a first side of said plate, and said first and second holes extend along first and second axes, respectively, that are non-orthogonally oriented to said lower surface of said plate to receive said bone fasteners positioned therethrough, said plate further including an anchor member adjacent said first opening and an anchor member adjacent said second opening, said anchor members extending from said lower surface, said anchor members each being orthogonally oriented to said lower surface and extending along an axis intersecting a respective one of said first and second hole axes, said anchor members being attached to said plate before fasteners are inserted through said first and second holes.

10. The system of claim 9, wherein said lower surface of said plate is structured for positioning along an antero-lateral portion of the first and second vertebrae with said first side extending medially along the first and second vertebrae and said second side extending laterally along the first and second vertebrae.

11. The system of claim 10, wherein plate is sized between said first and second sides so that said first and second sides are each offset to a first side of the sagittal plane of the first and second vertebrae when positioned along the antero-lateral portions thereof.

12. The system of claim 11, wherein said plate includes a first thickness between said upper and lower surfaces along said first side thereof that is less than a second thickness between said upper and lower surfaces along said second side thereof.

13. The system of claim 9, wherein said lower surface of said plate is concavely curved between said first and second sides and said upper surface of said plate is convexly curved between said first and second sides.

14. The system of claim 9, wherein said first and second hole axes extend in a direction parallel to a sagittal plane of the spinal column segment when said plate is positioned along the antero-lateral portion of the first and second vertebrae.

15. The system of claim 14, wherein said anchor members each include an elongated body and a pointed distal end.

16. The system of claim 15, wherein said elongated body includes a square cross-sectional shape and said distal end is pyramidally shaped.

* * * * *